US006803369B1

(12) United States Patent
Erskine et al.

(10) Patent No.: US 6,803,369 B1
(45) Date of Patent: Oct. 12, 2004

(54) COMPOUNDS AND METHODS FOR THE TREATMENT OF NEOPLASTIC DISEASE

(75) Inventors: Symon G. Erskine, Collegeville, PA (US); Michael Gwynn, Collegeville, PA (US); Neil David Pearson, Harlow (GB); Edwina Imogen Wilding, Collegeville, PA (US)

(73) Assignees: SmithKline Beecham Corporation, Philadelphia, PA (US); SmithKlineBeecham p.l.c., Brentford (GB)

( * ) Notice: Subject to any disclaimer, the term of this patent is extended or adjusted under 35 U.S.C. 154(b) by 0 days.

(21) Appl. No.: 09/912,483

(22) Filed: Jul. 25, 2001

Related U.S. Application Data
(60) Provisional application No. 60/220,635, filed on Jul. 25, 2000.

(51) Int. Cl.$^7$ ............................................. A61K 31/497
(52) U.S. Cl. ........................... 514/253.06; 514/253.07; 514/253.08; 514/311; 514/312; 514/313; 514/314
(58) Field of Search .................. 514/253.06, 253.07, 514/253.08, 311, 312, 313, 314

(56) References Cited

U.S. PATENT DOCUMENTS

| 3,133,061 | A | * | 5/1964 | Kirchner ..................... 540/597 |
| 4,108,998 | A | * | 8/1978 | Demerson et al. .......... 514/291 |
| 5,426,224 | A | * | 6/1995 | Lee et al. .................... 564/177 |
| 6,063,801 | A | * | 5/2000 | LaVoie et al. .............. 514/394 |
| 6,174,678 | B1 | * | 1/2001 | Menzel et al. ................. 435/6 |

FOREIGN PATENT DOCUMENTS

| WO | WO 99/37635 | 7/1999 |
| WO | WO/0043383 | 1/2000 |
| WO | WO 00/21948 | 4/2000 |
| WO | WO 00/21952 | 4/2000 |
| WO | WO/0078748 | 6/2000 |
| WO | WO/107432 | 7/2000 |
| WO | WO/107433 | 7/2000 |
| WO | PCT/EP02/05708 | 5/2001 |
| WO | WO/02/096907 | 5/2001 |
| WO | WO/0208224 | 7/2001 |
| WO | WO/03/010138 | 7/2001 |
| WO | WO/224684 | 9/2001 |
| WO | WO/0250040 | 12/2001 |
| WO | WO/0256882 | 1/2002 |
| WO | PCT/EP03/00823 | 1/2002 |
| WO | PCT/EP03/00824 | 1/2002 |

OTHER PUBLICATIONS

Le Bras et al. "La Détermination de la Chimiosensibilité de Plasmodium Falciparum" (1987) Annales de Pédiatrie, 34(5), 349–356.*

Girault et al., "Antimalarial, Antitrypanosomal, and Antileishmanial Activities and Cytotoxicity of Bis(9–amino–6–chloro–2–methoxyacridines): Influence of the Linker" (2000) J. Med. Chem., 43(14), 2646–2654.*

Couturier, et al., "Bacterial death by DNA gyrase poisoning", *Trends in Microbiology*, 6(7): 269–275 (1998).

Y. Pommier, "Diversity of DNA topoisomerases I and inhibitors", *Biochimie*, 80: 255–270 (1998).

Smith, et al., "Quinazoline Derivatives. II. Synthesis of 4–(4'–Diethylamino–1'–methylbutyl–amino)–6–methoxyquinazoline (SN 12,253)", *Journal of American Chemical Society*, 68: 1301–1303 (1946).

R.B. Merrifield, "Solid Phase Peptide Synthesis. I. the Synthesis of a Tetrapeptide", *Journal of American Chemical Society*, 85: 2149–2154 (1963).

Neil Osheroff, "Eukaryotic Topoisomerase II Characterization of Enzyme Turnover", *The Journal of Biological Chemistry*, 261(21): 9944–9950 (1985).

Drlica, et al., "DNA Gyrase, Topoisomerase IV, and the 4–Quinolones", *Microbiology and Molecular Biology Reviews*, 61(3): 377–392 (1997).

Neil Osheroff, "Biochemical Basis for the Interactions of Type I and Type II Topoisomerases with DNA", *Pharmacology & Therapeutics*, 41: 223–241 (1989).

D'Incalci, et al., "DNA–topoisomerase inhibitors", *Current Opinions in Oncology*, 5: 1023–1028 (1993).

Capranico, et al., "DNA sequence selectivity of topoisomerases and topoisomerase poisons", *Biochimica et Biophysica Acta*, 1400: 185–194 (1998).

Wessel, et al., "Human Small Cell Lung Cancer NYH Cells Selected for Resistance to the Bisdioxopiperazine Topoisomerase II Catalytic Inhibitor ICRF–187 Demonstrate a Functional R162Q Mutation in the Walker A Consensus ATP Binding domain of the α Isoform", *Cancer Research*, 59: 3442–3450 (1999).

Hiasa, et al., "Topoisomerase IV Can Support oriC DNA Replication in Vitro", *The Journal of Biological Chemistry*, 269(23): 16371–16375 (1994).

Fortune, et al., "Merbarone Inhibits the Catalytic Activity of Human Topoisomerase IIα by Blocking DNA Cleavage", *The Journal of Biological Chemistry*, 273(28): 17643–17650 (1998).

(List continued on next page.)

Primary Examiner—James H Reamer
(74) Attorney, Agent, or Firm—Andrea V. Lockenour; Edward R. Gimmi; Charles M. Kinzig

(57) ABSTRACT

A method of modulating the activity of a aberrant cell topoisomerase enzyme involving contacting the enzyme with a compound that inhibits enzyme-mediated cleavage of a polynucleotide substrate with which the enzyme is in complex. Pharmaceutical compositions containing such compounds may be used to treat neoplasias or to inhibit the growth of certain cancer cells. Screening methods can be employed to identify other compounds for these uses.

3 Claims, No Drawings

OTHER PUBLICATIONS

Chini, et al., "Regioalternating Selectivity in the Metal Salt Catalyzed Animolysis of Styrene Oxide", *Journal of Organic Chemistry*, 56: 5939–5942 (1991).

Anthony Maxwell, "Protein gates in DNA topoisomerase II", *Nature Structural Biology*, 3(2): 109–112 (1996).

Nishibata, et al., "Automatic Creation of Drug Candidate Structures Based on Receptor Structure. Starting Point for Artificial Lead Generation.", *Tetrahedron*, 47(43): 8985–8990 (1991).

Olland, et al., "Catalysis of ATP Hydrolysis by Two $NH_2$–terminal Fragments of Yeast DNA Topoisomerase II", *The Journal of Biological Chemistry*, 274(31): 21688–21694 (1999).

Roca, et al., "Antitumor bisdioxopiperazines inhibit yeast DNA topoisomerase II by trapping the enzyme in the form of a closed protein clamp", *Proceedings of the National Academy of Sciences USA*, 91: 1781–1785 (1994).

Stingl, et al., "Process for the preparation of 2–(S)–piperazinecarboxylic acid by continuous resolution via diastereomeric salt pairs", *Tetrahedron: Assymmetry*, 8(7): 979–982 (1997).

Anthony Maxwell, "DNA gyrase as a drug target", *Trends in Microbiology*, 5(3): 102–109 (1997).

Critchlow, et al., "DNA Cleavage Is Not Required for the Binding of Quinolone Drugs to the DNA Gyrase–DNA Complex", *Biochemistry*, 35: 7387–7393 (1996).

Capranico, et al., "DNA topoisomerase II poisons and inhibitors", *Cancer Chemotherapy and Biological Response Modifiers Annual 17*, Elsevier Science, Chapter 6, pp. 114–131 (1997).

U.S. patent application Ser. No. 09/912,610, Erskine et al., filed Jul. 2001.

U.S. patent application Ser. No. 10/199,933, Erskine et al., filed Jul. 2002.

U.S. patent application Ser. No. 60/391,700, Axten et al., filed Jun. 26, 2002.

U.S. patent application Ser. No. 60/391,710, Axten et. al., filed Jun. 26, 2002.

Le Bras et al. "La Détermination de la Chimosensibilité de Plasmodium Falciparum" (1987) Annales de Pédiatrie, 34(5), 349–356.

Girault et al., "Antimalarial, Antitrypanosomal, and Antileishmanial Activities and Cytotoxicity of Bis (9–amino–6–chloro–2–methoxyacridines): Influence of the Linker" (2000) J. Med. Chem., 43(14), 2646–2654.

Gellert, et al., (19776) *Proc. Natl. Acad. Sci. USA* (73)11, DNA gyrase: An Enzyme that Introduces Superhelical Turns into DNA, pp. 3872–3876.

Hammonds, T. and Maxwell, A., *Journal of Biogical Chemistry*, (272)51, "The DNA Dependence of the ATPase Activity of Human DNA Topoisomerase II∝*", pp. 32696–32703.

Kornberg and Baker, 1992, *DNA Replication*, $2^{nd}$ Ed., (Chapter 12—"Topoisomerases") ISBN 0–7167–2003–5.

* cited by examiner

COMPOUNDS AND METHODS FOR THE TREATMENT OF NEOPLASTIC DISEASE

This application claims the benifit of Provisional Application No. 60/220,635, filed Jul. 25, 2000.

FIELD OF THE INVENTION

The invention relates generally to novel methods of treating mammalian diseases using compounds that inhibit a biological activity of a topoisomerase enzymes.

BACKGROUND OF THE INVENTION

DNA topoisomerases are a group of enzymes present in all cells (both prokaryote and eukaryote) which are responsible for catalyzing topological changes in DNA. These enzymes have important functions for DNA replication, transcription and recombination, and have been shown to be essential for viability. Briefly, DNA topoisomerases supercoil and relax polynucleotides; they catalyze the reaction in which a polynucleotide, such as a double stranded DNA, wraps around the enzyme forming a complex therewith. The enzyme then catalyzes the cleavage of the double-stranded DNA and the passage of another DNA segment through the cleavage site, and then the relegation of the DNA at the cleavage site.

Eukaryotic topoisomerases are targets for antitumor agents. Some chemical agents, e.g., certain poisons and catalytic inhibitors, able to interfere with DNA topoisomerases have clinical efficacy as antitumor drugs. Many of these agents inhibit the topoisomerase at different sites, resulting in differential anticancer activity. [G. Capranico and M. Binaschi, (1998) Biochim et Biophs. Acta, 1400:185–1941. In particular, the quinolone group and the coumarin antibiotics, e.g., novobiocin and coumermycine A1 [A. Maxwell, (1997) "DNA Gyrase as a Drug Target", Trends in Microbiology, 5:102–109] are useful anti-bacterial drugs. DNA cleavage is not required for the binding of quinolone drugs to the gyrase-DNA complex [Critchlow S. E., and Maxwell A. (1996) Biochemistry, 35: 7387–7393], the antibacterial activity of the quinolone group of antibacterials is, however, predicated upon the ability of these compounds to induce gyrase-mediated DNA breakage. [Drlica, K. and Zhao, X. (1997) Microbiology and Molecular Biology Reviews, 61:377–392]. See, also, M. D'Incalci, (1993) Curr. Opin. Oncol., 5:1023–1028; Y. Pommier, (1988) Biochimie, 80:255–270; A. Maxwell, (1996) Nature Structural Biol., 3(2):109–112; G. Capranico et al, Chap. 6 in "Cancer Chemotherapy and Biological Response Modifiers Annual 17", H. M. Pinedo et al eds., 1997, Elsevier Science B. V.; and M. Couteurier et al, (1998) Trends in Microbiology, 6(7):269–275; Osheroff, J. Biol. Chem., 261:9944–9950 (1985); and Osheroff, Pharinac. Ther., 41:223–241 (1989)].

Among the inhibitors of human topoisomerase II are merbarone, and the bis(2,6-dioxopiperazines) such as ICR-193. While these agents do not induce topoisomerase dependent cleavage of DNA, their mechanism of action is different from the subject of this invention. Merbarone inhibits the catalytic activity of human topoisomerase 11 by blocking DNA cleavage, however DNA binding studies showed that the apparent Kd's (dissociation constants) for enzyme to DNA binding were not substantially affected by the inhibitor, thus not consistent with the stabilisation of a ternary complex (Fortune J. M., and Osheroff N. (1998) J. Biol. Chem. 273 17643–50). ICRF-193 blocks ATP hydrolysis in eucaryotic topoisomerase II, an action that traps the enzyme on the DNA in a closed clamp form, preventing the protein clamp from opening, and thereby preventing release of DNA (Roca et al PNAS 91 1781–5). Point mutations, causing resistance to these drugs, however map to the ATPase of topoisomerase II (Wessel et al 1999 Cancer Research 59 3442–50). Additionally, ICRF-193 has been shown to directly bind to the dimerized ATPase domains of the yeast enzyme (Olland S., and Wang J. C. 1999 J. Biol Chem 274 21688–94).

Some of the presently used compounds for antitumor treatment based on inhibition of topoisomerases have disadvantages, such as ineffectiveness against certain cell types due to resistance mechanisms associated with their mode of action, unwanted toxicity and mutagenicity, particularly in view of the DNA cleavage activity of these compounds. Thus, there exists a need in the art for novel anti-tumor compounds, pharmaceutical compositions and methods of use thereof, especially compounds that do not exhibit DNA cleavage activity. Such compounds, compositions and methods are provided by the present invention.

SUMMARY OF THE INVENTION

In one aspect, the invention provides a method of modulating the activity of a type II topoisomerase enzyme of an aberrant cell comprising contacting the aberrant cell enzyme with a compound that inhibits the enzyme-mediated cleavage of a polynucleotide substrate. In one embodiment of this method, the compound forms a stable or transient non-covalent complex, preferably a ternary complex, with a topoisomerase enzyme and a substrate, for example a polynucleotide, particularly DNA. In another embodiment of this method, the compound inhibits the formation of the complex between a substrate and the enzyme. The aberrant cell which employs this enzyme for replication may be from a eukaryote, particularly a mammal, and especially a human. The polynucleotide substrate may be any DNA, RNA or DNA-RNA hybrid. In one embodiment, the method involves contacting an enzyme, or an aberrant cell, with the compound that inhibits replication of, or kills, the aberrant cell carrying the enzyme. Such contacting step can occur in vitro, in vivo in a mammal containing the aberrant cell or ex vivo in mammalian tissue outside of the body.

In another aspect, the invention provides a pharmaceutical composition comprising a compound that inhibits, arrests, or otherwise alters, the aberrant cell type II topoisomerase enzyme-mcdiated cleavage of a polynucleotide substrate in a pharmaceutically or physiologically acceptable carrier. In one embodiment, the compound is one that is identified by the assays described herein. Preferably, the composition has anti-tumor, and may contain other agents and/or excipients useful in the treatment of aberrant cell diseases, particularly in mammals, and especially in humans.

In yet a further aspect, the invention provides a method for treating a mammal or mammalian tissue comprising aberrant cells having a type II topoisomerase enzyme, the method comprising administering to the mammal an effective amount of an above-described pharmaceutical composition. This method involves administering the composition by a route, such as intravenous, oral, intradermal, transdermal, intraperitoneal, intramuscular, subcutaneous, by inhalation and mucosal. Preferably this method is useful for treating such diseases in a human, or in human tissue.

In another aspect, the invention provides a method for identifying an anti-tumor compound comprising screening the compound for the ability to inhibit, or otherwise alter, an aberrant cell type II topoisomerase-mediated cleavage of a polynucleotide substrate. In one embodiment, the method includes determining that a compound forms a high molecular weight higher order complex, such as a ternary complex, with the enzyme and a polynucleotide substrate.

In a preferred embodiment a method is provided for identifying an anti-tumor compound comprising screening the compound for the ability to inhibit, or otherwise alter, an aberrant cell type II topoisomerase-mediated cleavage of a polynucleotide substrate in the present of another compound. In this method compounds that potentiate the antagonism of the aberrant cell type II topoisomerase-mediated cleavage may be identified.

In another embodiment a compound may be screened against both a mammalian topoisomerase and a pathogen topoisomerase or gyrase, such as prokaryotic topoisomerase or gyrase, to identify a compound that inhibits and/or binds to both the mammalian topoisomerase and the pathogen topoisomerase or gyrase.

In another aspect of the invention are compounds of the invention not known in the art prior to the filing date of this application or an application to which this application claims benefit of priority.

In one embodiment, the method includes determining that a compound forms a high molecular weight higher order complex, such as a ternary complex, with the enzyme and a polynucleotide substrate.

In another embodiment, the determining step comprises adding a reaction mixture comprising in a buffer, a test compound, the enzyme, and the polynucleotide substrate to a size exclusion chromatographic column; and monitoring the fractions eluting from the chromatographic column to detect the fraction containing the higher order complex, such as a ternary complex.

In another embodiment, the screening method involves detecting an intact complex comprising the polynucleotide and the enzyme. Such a screening method involves reacting a test compound with the enzyme and polynucleotide substrate; quenching the reaction with a quenching compound, such as a denaturant; and performing a detection analysis, such as a gel analysis, to detect if the polynucleotide is intact or altered.

In still another embodiment, the screening method involves performing a replication blockage assay.

In a further aspect, the invention provides a compound identified by any of the above screening methods.

In yet a further preferred embodiment the compound comprises a moeity that binds both subunits of a topoisomerase, or which compound comprises a moiety that binds more than one topoisomerase homo- or hetero-dimers, or which compound binds more than one topoisomerase homo- or hetero-dimer.

In still an additional embodiment, the invention provides a method for modifying a surface comprising contacting a surface with a composition comprising a compound which inhibits an aberrant cell type II topoisomerase-mediated cleavage of a polynucleotide substrate. The surface may be a biological tissue, in or outside of an individual. The method's contacting step comprises administering a suitable modifying dosage of the composition by means selected from the group consisting of coating, spraying, implanting, or soaking, among others.

In one aspect, the invention provides a method of modulating the activity of a mammalian type II topoisomerase enzyme comprising contacting the enzyme with a compound that inhibits enzyme-mediated cleavage of a polynucleotide substrate. In one embodiment, this method permits the compound to form a transient or stable non-covalent higher order structure, such as a ternary complex, comprising the enzyme, the polynucleotide, and the compound. In another embodiment, the method involves preventing the formation of the enzyme-polynucleotide complex, or comprising the enzyme and the compound. In another embodiment, the method involves preventing the formation of the enzyme-polynucleotide complex. The mammalian enzymes are preferably human or domestic animal in origin. The polynucleotide substrate is a polynucleotide, such as, DNA, RNA or a DNA-RNA hybrid, including but not limited to polynucleotides with modified bases. In a preferred embodiment, the enzyme is associated with a mammalian disease, and the method inhibits the progression of the disease, e.g., cancer. Preferably the method inhibits replication, proliferation or differentiation of cancer cells. The contacting step of the method can occur in vitro, in vivo in a mammal, or ex vivo on mammalian tissue.

In another aspect, the method provides a pharmaceutical composition comprising a compound that inhibits the mammalian type II topoisomerase enzyme-mediated cleavage of a polynucleotide substrate in a pharmaceutically or physiologically acceptable carrier. In one embodiment, the compound is a compound described herein. In another embodiment, the compound is one identified by the screening assays described herein. The composition preferably has anti-cancer activity, and can contain other conventional anticancer agents or excipients normally useful in anticancer compositions.

In still another aspect, the invention provides a method for treating a disease, e.g., cancer, in a mammal characterized by the abnormal behavior of a mammalian type II topoisomerase enzyme comprising administering to the mammal having the disease an effective amount of a pharmaceutical composition described above. According to the method, the composition is administered by a route, such as intravenous, oral, intradermal, transdermal, intraperitoneal, intramuscular, subcutaneous, by inhalation and mucosal in a dosage appropriate for the disease, patient, e.g., human, and route of administration.

In yet another aspect, the invention provides a method for identifying a compound useful to treat mammalian diseases characterized by the aberrant presence or activity of a mammalian type II topoisomerase comprising screening the compound for the ability to inhibit a mammalian type II topoisomerase-mediated cleavage of a polynucleotide substrate. Preferably the compound is an anticancer compound. One method step involves determining that the compound forms a high molecular weight ternary complex with the enzyme and the polynucleotide substrate. In one embodiment such a determining step comprises adding a reaction mixture comprising in a buffer, a test compound, the enzyme, and the polynucleotide substrate to a size exclusion chromatographic column; and monitoring the fractions eluting from the chromatographic column to detect the fraction containing the ternary complex.

In another embodiment of a screening method, a step is performed to detect an intact complex comprising the polynucleotide and the enzyme. For example, a test compound is reacted with the enzyme and polynucleotide substrate; the reaction quenched with a denaturant; and a gel analysis performed to indicate if the polynucleotide is intact. In still another embodiment of a screening method, a screening step comprises a replication blockage assay.

In still another aspect, the invention provides a method for screening for an anticancer compound comprising the steps of: obtaining the crystal structure of a compound that inhibits the mammalian type II topoisomerase-mediated cleavage of a polynucleotide substrate; and performing computer analysis to design or select from among test compounds, a compound having a substantially similar binding characteristics.

In one embodiment, the method comprises the step of exposing the compound having the substantially sinmilar crystal structure to a sample of cancer cells, and observing the cells for inhibition of replication, wherein the occurrence of inhibition is indicative of an anticancer compound.

In yet a further embodiment of the invention, a method of treatment is provide comprising the step of contacting the patient to be treated with a composition comprising compound of the invention and another antineoplastic agent, preferably an antineoplastic agent that acts by a mechanism other than topoisomerase.

Another embodiment of the invention provides a composition comprising compound of the invention and another antineoplastic agent, preferably an antineoplastic agent that acts by a mechanism other than topoisomerase.

In yet a further aspect, the invention provides a compound identified by the methods described above.

Other aspects and advantages of the present invention are described further in the following detailed description of the preferred embodiments thereof.

DETAILED DESCRIPTION OF THE INVENTION

The present invention provides compositions and methods for identifying and using compounds that exhibit a novel mechanism of anti-aberrant cell and/or anticancer activity, based upon inhibition of aberrant cell and mammalian type II topoisomerases by a previously undescribed mechanism. Unlike other such inhibitors, compounds of this invention inhibit aberrant cell growth or tumor cell growth by inhibiting the type II topoisomerase enzyme-mediated cleavage of a polynucleotide substrate by forming a non-covalent ternary complex among the topoisomerase, the substrate and the compound. The cleavage of the polynucleotide from its complex with the topoisomerase is one of the normal biological activities of these type II topoisomerases.

COMPOUNDS OF THIS INVENTION

As stated above, the compounds embraced by this invention include all compounds that can modulate the activity of a type II topoisomerase enzyme by inhibiting the enzyme-mediated cleavage of the polynucleotide with which that enzyme forms a complex. This inhibiting activity of compounds of this invention includes stabilizing the complex formed between the enzyme and the uncleaved polynucleotide by forming a non-covalent ternary complex between the compound, the enzyme and the polynucleotide. Alternatively, the inhibiting activity includes preventing the formation of the enzyme-uncleaved polynucleotide complex, so that there is no associated polynucleotide for the enzyme to cleave. Also included in the invention are compounds that act together to modulate the activity of a type II topoisomerase enzyme, such as by coordination, synergy, or other combination effects.

In still another preferred embodiment the enzyme which is the target of the inhibition by the compounds of this invention is a mammalian type II topoisomerase enzyme, and more preferably, the human enzyme, which is associated with various forms of cancer and solid tumors. In another embodiment, the enzyme may be that of a domestic animal, e.g., canine or feline, or other valuable animals such as equines or certain farm or stock animals, which may be treated for such diseases.

As stated above, these enzymes normally complex with a polynucleotide substrate in the cell, e.g., an aberrant cell, preferably a transformed, hyperplastic or cancer cell. The complexed polynucleotide substrate of the topoisomerase enzyme can be DNA, RNA or a DNA-RNA hybrid. The polynucleotide may also be linear, supercoiled or relaxed. In the examples below, the exemplary substrate is pBR322 DNA. One of skill in the art may select any suitable polynucleotide substrate for use in the assays below which are performed to identify and select novel test compounds demonstrating the topoisomerase modulating activity described herein. Without interference, the normal topoisomerase activity is to cleave and reseal the complexed polynucleotide as part of the enzyme's essential function to keep the cancer cell viable and replicating. The compounds of this invention prevent or inhibit that cleavage, and thus inhibit the growth and replication of the aberrant cell or cancer cell in which the enzyme is present.

Because the inventors are the first to associate the ability to inhibit the polynucleotide cleavage by this mechanism (stabilisation of a non-covalent enzyme-DNA-inhibitor ternary complex by contacting the enzymes DNA cleavage reunion domains) with anti-aberrant cell and anti-tumor action, the compounds encompassed by this invention include compounds now identified by the inventors as having this inhibitory action, as well as compounds which may be identified by the screening methods described herein.

These compounds include, for example the compounds described in WO99/137635, WO00/21948 and WO00/21952,as well as a compound of formula (Ia) or a pharmaceutically acceptable derivative thereof:

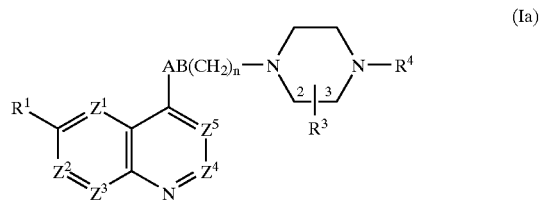

(Ia)

wherein:
one of $Z^1$, $Z^2$, $Z^3$, $Z^4$ and $Z^5$ is N, one is $CR^{1a}$ and the remainder arc CH, or one of $Z^1$, $Z^2$, $Z^3$, $Z^4$ and $Z^5$ is $CR^{1a}$ and the remainder are CH;
$R^1$ is selected from hydroxy; $(C_{1-6})$ alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$ alkylsulphonyloxy; $(C_{1-6})$alkoxy-substituted $(C_{1-6})$alkyl; halogen; $(C_{1-6})$alkyl; $(C_{1-6})$alkylthio; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups, or when one of $Z^1$, $Z^2$, $Z^3$, $Z^4$ and $Z^5$ is N, $R^1$ may instead be hydrogen;
$R^1$a is selected from H and the groups listed above for $R^1$;
$R^3$ is hydrogen; or
$R^3$ is in the 2- or 3-position and is:

carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{1-6})$alkenylsulphonyl, $(C_{1-6})$ alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione4-yl;2, 4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $R^3$ is in the 2- or 3-position and is $(C_{1-4})$alkyl or ethenyl substituted with any of the groups listed above for $R^3$ and/or 0 to 3 groups $R^{12}$ independently selected from:

thiol; halogen; $(C_{1-6})$alkylthio; trifluoromethyl; azido; $(C_{1-6})$alkoxycarbonyl; $(C_{1-6})$alkylcarbonyl; $(C_{2-6})$ alkenyloxycarbonyl; $(C_{2-6})$alkenylcarbonyl; hydroxy optionally substituted by $(C_{1-6})$alkyl, $(C_{2-6})$alkenyl, $(C_{1-6})$ alkoxycarbonyl, $(C_{1-6})$alkylcarbonyl, $(C_{2-6})$ alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$ alkenylcarbonyl; amino optionally mono- or disubstituted by $(C_{1-6})$alkoxycarbonyl, $(C_{1-6})$alkylcarbonyl, $(C_{2-6})$ alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$ alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$ aminosulphonyl wherein the amino group is optionally substituted by $(C_{1-6})$alkyl or $(C_{2-6})$alkenyl; provided that when $R^3$ is disubstituted with hydroxy or amino and carboxy containing substituents these may optionally together form a cyclic ester or arnide linkage, respectively;

wherein $R^{10}$ is selected from $(C_{1-4})$alkyl; $(C_{2-4})$alkenyl; aryl; a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{1-6})$alkenylsulphonyl, $(C_{1-6})$ alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl or $(C_{2-6})$alkenyl; cyano; or tetrazolyl;

$R^4$ is a group —$CH_2$-$R^5$ in which $R^5$ is selected from:

$(C_{3-12})$alkyl; hydroxy$(C_{3-12})$alkyl; $(C_{1-12})$alkoxy$(C_{3-12})$ alkyl; $(C_{1-12})$alkanoyloxy$(C_{3-12})$alkyl; $(C_{3-6})$cycloalkyl $(C_{3-12})$alkyl; hydroxy-, $(C_{1-12})$alkoxy- or $(C_{1-12})$ alkanoyloxy-$(C_{3-6})$cycloalkyl$(C_{3-12})$alkyl;cyano$(C_{3-12})$ alkyl; $(C_{2-12})$alkenyl; $(C_{2-12})$alkynyl; tetrahydrofuryl; mono- or di-$(C_{1-12})$alkylamino$(C_{3-12})$alkyl; acylamino $(C_{3-12})$alkyl; $(C_{1-12})$alkyl- or acyl-aminocarbonyl$(C_{3-12})$alkyl; mono or di-$(C_{1-12})$ alkylamino(hydroxy)$(C_{3-12})$alkyl; optionally substituted phenyl$(C_{1-12})$alkyl, phenoxy$(C_{1-12})$alkyl or phenyl(hydroxy)$(C_{1-12})$alkyl; optionally substituted diphenyl$(C_{1-2})$alkyl; optionally substituted phenyl$(C_{2-3})$alkenyl; optionally substituted benzoyl or benzoyl$(C_{1-3})$alkyl; optionally substituted heteroaryl or heteroaryl$(C_{1-12})$alkyl;and optionally substituted heteroaroyl or heteroaroylmethyl;

n is 0,1 or 2;

AB is $NR_{11}CO,CO$—$CR^8R^9$ or $CR^6R^7$—$CR^8R^9$ or when n is 1 or 2, AB may instead be O—$CR^8R^9$ or $NR^{11}$—$CR^8R^9$, or when n is 2 AB may instead be $CR^6R^7$—$NR^{11}$ or $CR^6R^7$—O, provided that when n is 0, B is not CH(OH), and wherein:

each of $R^6$ and $R^7$ $R^8$ and $R^9$ is independently selected from: H; thiol; $(C_{1-6})$alkylthio; halo; trifluoromethyl; azido; $(C_{1-6})$alkyl; $(C_{2-6})$alkenyl; $(C_{1-6})$ alkoxycarbonyl; $(C_{1-6})$alkylcarbonyl; $(C_{2-6})$ alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{1-6})$alkenyl; or $R^6$ and $R^8$ together represent a bond and $R^7$ and $R^9$ are as above defined; and each $R^{11}$ is independently H, trifluoromethyl, $(C_{1-6})$alkyl, $(C_{1-6})$alkenyl, $(C_{1-6})$alkoxycarbonyl, $(C_{1-6})$alkylcarbonyl, aminocarbonyl wherein the amino group is optionally substituted by $(C_{1-6})$ alkoxycarbonyl, $(C_{1-6})$alkylcarbonyl, $(C_{1-6})$ alkenyloxycarbonyl, $(C_{2-6})$alkenylcarbonyl, $(C_{1-6})$ alkyl or $(C_{1-6})$alkenyl and optionally further substituted by $(C_{1-6})$alkyl or $(C_{1-6})$alkenyl;

or where one of $R^3$ and $R^6$, $R^7$, R8 or $R^9$ contains a carboxy group and the other contains a hydroxy or amino group they may together form a cyclic ester or amide linkage.

The term "heterocyclic" as used herein includes aromatic and non-aromatic, single and fused, rings suitably containing up to four hetero-atoms in each ring selected from oxygen, nitrogen and sulphur, which rings may be unsubstituted or substituted by, for example, up to three groups selected from optionally substituted amino, halogen, $(C_{1-6})$ alkyl, $(C_{1-6})$alkoxy, halo$(C_{1-6})$alkyl, hydroxy, carboxy, carboxy salts, carboxy esters such as $(C_{1-6})$alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include $(C_{1-6})$alkyl optionally substituted by hydroxy, $(C_{1-6})$alkoxy, thiol, $(C_{1-6})$alkylthio, halo or trifluoromethyl, and amino-protecting groups such as acyl or $(C_{1-6})$ alkylsulphonyl groups.

The term 'heteroaryl' includes the aromatic heterocyclic groups referred to above. Examples of heteroaryl groups include pyridyl, triazolyl, tetrazolyl, indolyl, thienyl, isoimidazolyl, thiazolyl, furanyl,quinolinyl, imidazolyl, 1,3-dihydro-2-oxo-benzimidazolyl and benzothienyl.

When used herein the term 'aryl', includes phenyl and naphthyl, each optionally substituted with up to five, preferably up to three, groups selected from halogen, mercapto, $(C_{1-6})$alkyl, phenyl, $(C_{1-6})$alkoxy, hydroxy$(C_{1-6})$alkyl, mercapto $(C_{1-6})$alkyl, halo$(C_{1-6})$alkyl, hydroxy, optionally substituted amino, nitro, cyano, carboxy, (C$_{1-6}$) alkylcarbonyloxy, (C$_{1-6}$)alkoxycarbonyl, formyl, or (C$_{1-6}$) alkylcarbonyl groups.

The term 'acyl' includes (C$_{1-6}$)alkoxycarbonyl, formyl or (C$_{1-6}$) alkylcarbonyl group.

A process for preparing compounds of formula (Ia), or a pharmaceutically acceptable derivative thereof, comprises:
(a) reacting a compound of formula (IIa) with a compound of formula (IIIa):

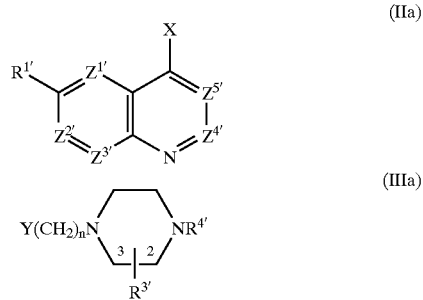

(IIa)

(IIIa)

wherein Z$^1$, Z$^2$, Z$^3$, Z$^4$ and Z$^5$, m, n, R$^1$, R$^3$ and R$^4$ are as defined in formula (Ia), and X and Y may be the following combinations:
(i) X is M and Y is CH$_2$CO$_2$R$^x$,CH$_2$CHO or CH$_2$COW
(ii) X is CO$_2$R$^y$ and Y is CH$_2$CO$_2$R$^x$
(iii) one of X and Y is CH=SPh$_2$ and the other is CHO
(iv) X is CH$_3$ and Y is CHO
(v) X is CH$_3$ and Y is CO$_2$R$^x$
(vi) X is CH$_2$CO$_2$R$^y$ and Y is CO$_2$R$^x$
(vii) X is CH=PR$^z$$_3$ and Y is CHO
(viii) X is CHO and Y is CH=PR$^z$$_3$
(ix) X is halogen and Y is CH=CH$_2$
(x) one of X and Y is COW and the other is NHR$^{11'}$ or NCO
(xi) one of X and Y is (CH$_2$)$_p$-W and the other is (CH$_2$)$_q$ NHR$_{11'}$ or (CH$_2$)$_q$OH
(xii) one of X and Y is CHO and the other is NHR$^{11'}$,
or where n=0
(xiii) X is A—B—(CH$_2$)$_n$-W or A-B-(CH$_2$)$_{n-1}$—CHO and Y is H
(xiv) X is NCO and Y is H
(xv) X is CH$_3$ and Y is H
(xvi) X is COCH$_2$W and Y is H
(xvii) X is CH=CH$_2$ and Y is H
(xviii) X is oxirane and Y is H
to in which W is a leaving group, R$^x$ and R$^y$ are (C$_{1-6}$)alkyl and R$^z$ is aryl or (C$_{1-6}$)alkyl;
or
(b) reacting a compound of formula (IIa) with a compound of formula (IIIa.b):

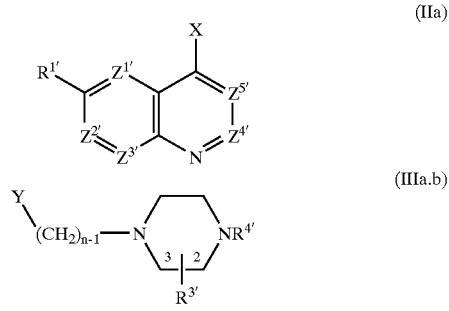

(IIa)

(IIIa.b)

wherein Z$^1$,Z$^2$,Z$^3$,Z$^4$ and Z$^5$,m,n,R$^1$,R$^3$ and R$^4$ are as defined in formula (Ia),X is CH$_2$NHR$^{11'}$ and Y is CHO or COW;

in which Z$^{1'}$,Z$^{2'}$,Z$^{3'}$,Z$^{4'}$,Z$^{5'}$,R$^{11'}$,R$^{1'}$, R$^{3'}$ and R$^{4'}$ are Z$^1$,Z$^2$, Z$^3$,Z$^4$,Z$^5$,R$^{11}$,R$^1$,R$^3$ and R$^4$ or groups convertible thereto, and thereafter optionally or as necessary converting Z$^{1'}$,Z$^{2'}$,Z$^{3'}$,Z$^{4'}$,Z$^{5'}$,R$^{11'}$,R$^{1'}$,R$^{3'}$ and R$^{4'}$ to Z$^1$,Z$^2$, Z$^3$,Z$^4$,Z$^5$,R$^{11'}$R$^1$,R$^3$ and R$^4$, converting A-B to other A-B, interconverting Z$^1$,Z$^2$,Z$^3$,Z4,Z$^5$, R$^{11}$,R$^1$,R$^3$ and/or R$^4$ and forming a pharmaceutically acceptable derivative thereof.

Compounds of formulae (IIa), (IIIa) and (IIIa.b) are known compounds, (see for example Smith et al, *J. Amer. Chem. Soc.*, 1946, 68, 1301) or prepared analogously.

WO99/37635, incorporated herein by reference, discloses compounds of formula (Ib) or a pharmaceutically acceptable derivative thereof and process for their preparation:

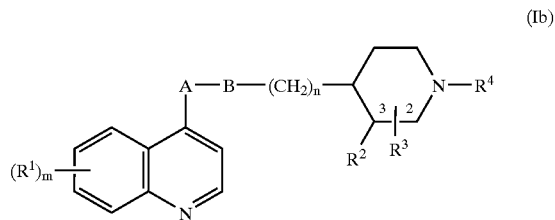

(Ib)

wherein:
m is 1 or2
each R$^1$ is independently hydroxy; (C$_{1-6}$) alkoxy optionally substituted by (C$_{1-6}$)alkoxy, amino, piperidyl, guanidino or amidino optionally N-substituted by one or two (C$_{1-6}$)alkyl, acyl or (C$_{1-6}$)alkylsulphonyl groups, NH$_2$CO, hydroxy, thiol, (C$_{1-6}$)alkylthio, heterocyclylthio, heterocyclyloxy, arylthio, aryloxy, acylthio, acyloxy or (C$_{1-6}$)alkylsulphonyloxy; (C$_{1-6}$) alkoxy-substituted (C$_{1-6}$)alkyl; halogen; (C$_{1-6}$)alkyl; (C$_{1-6}$)alkylthio; nitro; azido; acyl; acyloxy; acylthio; (C$_{1-6}$)alkylsulphonyl; (C$_{1-6}$)alkylsulphoxide; arylsulphonyl; arylsulphoxide or an amino, piperidyl, guanidino or amidino group optionally N-substituted by one or two (C$_{1-6}$)alkyl, acyl or (C$_{1-6}$)alkylsulphonyl groups;
either R$^2$ is hydrogen; and
R$^3$ is in the 2- or 3-position and is hydrogen or (C$_{1-6}$)alkyl or (C$_{2-6}$)alkenyl optionally substituted with 1 to 3 groups selected from:
thiol; halogen; (C$_{1-6}$)alkylthio; trifluoromethyl; azido; (C$_{1-6}$)alkoxycarbonyl; (C$_{1-6}$)alkylcarbonyl; (C$_{2-6}$) alkenyloxycarbonyl; (C$_{2-6}$)alkenylcarbonyl; hydroxy optionally substituted by (C$_{1-6}$)alkyl, (C$_{2-6}$)alkenyl, (C$_{1-6}$)alkoxycarbonyl, (C$_{1-6}$)alkylcarbonyl, (C$_{2-6}$) alkenyloxycarbonyl, (C$_{2-6}$)alkenylcarbonyl or aminocarbonyl wherein the amino group is optionally substituted by (C$_{1-6}$)alkyl, (C$_{2-6}$)alkenyl, (C$_{1-6}$) alkylcarbonyl or (C$_{2-6}$)alkenylcarbonyl; amino optionally mono- or disubstituted by (C$_{1-6}$)alkoxycarbonyl, (C$_{1-6}$)alkylcarbonyl, (C$_{2-6}$)alkenyloxycarbonyl, (C$_{2-6}$) alkenylcarbonyl, (C$_{1-6}$)alkyl, (C$_{2-6}$)alkenyl, (C$_{1-6}$) alkylsulphonyl, (C$_{2-6}$)alkenylsulphonyl or aminocarbonyl wherein the amino group is optionally substituted by (C$_{1-6}$)alkyl or (C$_{2-6}$)alkenyl; aminocarbonyl wherein the amino group is optionally substituted by (C$_{1-6}$)alkyl, hydroxy(C$_{1-6}$)alkyl, aminocarbonyl(C$_{1-6}$) alkyl, (C$_{2-6}$)alkenyl, (C$_{1-6}$)alkoxycarbonyl, (C$_{1-6}$) alkylcarbonyl, (C$_{2-6}$)alkenyloxycarbonyl or (C$_{2-6}$) alkenylcarbonyt and optionally further substituted by (C$_{1-6}$)atkyl, hydroxy(C$_{1-6}$)alkyl, aminocarbonyl(C I)alkyl or (C$_{2-6}$)alkenyl; oxo; (C$_{1-6}$)alkylsulphonyl; (C$_{2-6}$)alkenylsulphonyl; or aminosulphonyl wherein the amino group is optionally substituted by $(C_{1-6})$alkyl or $(C_{2-6})$alkenyl; or $R^3$ is in the 3-position and $R^2$ and $R^3$ together are a divalent residue $=CR^{5'}R^{6'}$ where $R^{5'}$ and $R^{6'}$ are independently selected from H, $(C_{1-6})$alkyl, $(C_{2-6})$alkenyl, aryl$(C_{1-6})$alkyl and aryl$(C_{2-6})$alkenyl, any alkyl or alkenyl moiety being optionally substituted by 1 to 3 groups selected from those listed above for substituents on $R^3$;

$R^4$ is a group —$CH_2$-$R^5$ in which $R^5$ is selected from: $(C_{3-12})$alkyl; hydroxy$(C_{3-12})$alkyl; $(C_{1-12})$alkoxy$(C_{3-12})$alkyl; $(C_{1-12})$alkanoyloxy$(C_{3-12})$alkyl; $(C_{3-6})$cycloalkyl $(C_{3-12})$alkyl; hydroxy-, $(C_{1-12})$alkoxy- or $(C_{1-12})$alkanoyloxy-$(C_{3-6})$cycloalkyl$(C_{3-12})$alkyl; cyano$(C_{3-12})$alkyl; $(C_{1-12})$alke $(C_{2-12})$alkynyl; tetrahydrofuryl; mono- or di-$(C_{1-12})$alkylamino$(C_{3-12})$alkyl; acylamino$(C_{3-12})$alkyl; $(C_{1-12})$alkyl- or acylaminocarbonyl$(C_{3-12})$alkyl; mono- or di-$(C_{1-12})$alkylamino(hydroxy) $(C_{3-12})$alkyl; optionally substituted phenyl$(C_{1-2})$alkyl, phenoxy$(C_{1-2})$alkyl or phenyl (hydroxy)$(C_{1-12})$alkyl; optionally substituted diphenyl $(C_{1-2})$alkyl; optionally substituted phenyl$(C_{2-3})$alkenyl; optionally substituted benzoyl or benzoylmethyl; optionally substituted heteroaryl$(C_{1-12})$alkyl;and optionally substituted heteroaroyl or heteroaroylmethyl;

n is 0, 1 or 2;

A is $NR^{11}$,O,S(O)$_x$ or $CR^6R^7$ and B is $NR^{11}$,O,S(O)$_x$ or $CR^8R^9$ where x is 0, 1 or 2 and wherein:

each of $R^6$ and $R^7$ $R^8$ and $R^9$ is independently selected from: H; thiol; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{1-6})$alkenyl;

or $R^6$ and $R^8$ together represent a bond and $R^7$ and $R^9$ are as above defined;

or $R^6$ and $R^8$ together represent -O- and $R^7$ and $R^9$ are both hydrogen;

or $R^6$ and $R^7$ or $R^8$ and $R^9$ together represent oxo;

and each $R^{11}$ is independently H, trifluoromethyl, $(C_{1-6})$alkyl, $(C_{1-6})$alkenyl, $(C_{1-6})$alkoxycarbonyl, $(C_{1-6})$alkylcarbonyl, aminocarbonyl wherein the amino group is optionally substituted by $(C_{1-6})$alkoxycarbonyl, $(C_{1-6})$alkylcarbonyl, $(C_{1-6})$alkenyloxycarbonyl, $(C_{2-6})$alkenylcarbonyl, $(C_{1-6})$alkyl or $(C_{1-6})$alkenyl and optionally further substituted by $(C_{1-6})$alkyl or $(C_{1-6})$alkenyl;

provided that A and B cannot both be selected from $NR^{11}$,O and S(O)$_x$ and when one of A and B is CO the other is not CO, O or S(O)$_x$.

Specific embodiments of compounds useful in this invention include the following compounds:

SB208717:[3R,4R]-3-Ethyl-1-heptyl4-[3-(R,S)-hydroxy-3-(6-methoxyquinolin-4-yl) propyl]piperidine (Example 4 of WO99/37635);

SB291665:[3R,4R]-1-Heptyl-3-(1-(R)-hydroxyethyl)-4-[3-(6-methoxyquinolin-4-yl)propyl]piperidine (Example 85 of WO99/37635,first-mentioned diastereomer);

SB362569:[3R,4R]-1-Heptyl-3-hydroxymethyl-4-[3-(6-methoxyquinolin-4-yl)propyl]piperidine (Example 87 of WO99/37635);

SB366676 [2S]-1-Heptyl-4-[2-(R)-hydroxy-2-(6-methoxyquinolin-4-yl)ethyl]-2-hydroxymethylpiperazine;

SB369890 [2S]-2-Carboxymethyl-1-heptyl-4-[2-(R,S)-hydroxy-2-(6-methoxyquinolin-4-yl)ethyl]piperazine trihydrochloride (Exaample 4,below); and SB414468 1 -Hydroxyheptyl-4-[2-(R)-hydroxy-2-(6-methoxyquinolin-4-yl)ethyl]piperazine (Example 5 below), among others.

Other compounds of this invention are identified by screening for the ability to inhibit an aberrant cell or mammalian type II topoisomerase-mediated cleavage of a polynucleotide substrate from a ternary complex formed by the compound, the topoisomerase and the polynucleotide substrate. The term "inhibition" is also used to include stabilizing the complex formed between the type II topoisomerase and the uncleaved polynucleotide or preventing the formation of the type II topoisomerase-uncleaved polynucleotide complex.

As used herein "aberrant cell" means a eukaryotic cell that is transformed, neoplastic, cancerous, correlating with or obtained from a cancer or tumor, having a ploidy that is non-integer or greater than 2, having abnormal growth or differentiation characteristics, or displaying cancer cell markers.

One screening method involves determining that the compound forms a high molecular weight ternary complex with the enzyme and the polynucleotide. Such a screening step employs a physical method of determination, such as size exclusion chromatography with mass spectroscopy detection. According to this screening step a reaction mixture is formed by combining a sufficient amount of a test compound with a sufficient amount of the enzyme and the polynucleotide in a suitable buffer and allowing this mixture to react for a sufficient time to permit formation of the ternary complex, if one is to form. For such an assay a suitable amount of the test compound is between about 50 nM and 4 µM; a suitable amount of the enzyme is between about 10 nM and 200 nM; and a sufficient reaction time is greater than about 15 minutes. A suitable buffer for this reaction would include saline, buffered saline, trishydroxymethylaminomethane hydrochloride.

This reaction mixture is then applied to a size exclusion chromatographic column in which the test compound will normally only elute in the high molecular weight fraction, this separation could also be performed by ultrafiltration, dialysis or centrifugation. That is, the test compound will only elute if it has formed a high molecular weight ternary complex with the polynucleotide and the topoisomerase. By "high molecular weight" in this context is meant a complex of greater than about 230 kDa, typically between about 230 to 2000 kDa. The fractions are monitored by a conventional detection system, such as mass spectroscopy, to determine in which fraction the high molecular weight complex elutes from the chromatographic column. Other forms of detection, such as UV or fluorescence, may also be used in this screening step. By the use of controls in which the individual components of the complex, e.g., the enzyme or the polynucleotide, are omitted from the reaction mixture, it can be determined whether or not the test compound binds very weakly or not at all to the enzyme alone, but nevertheless enters into a ternary complex with the enzyme and polynucleotide.

In another embodiment of a method to identify a compound useful in the this invention, the screening assay employs a step to demonstrate that the polynucleotide in the ternary complex is uncleaved. Since the normal function of a topoisomerase is to cleave and reseal the polynucleotide substrate, and the compounds of this invention operate to inhibit this process at a stage with the polynucleotide sequence is unbroken, a "breakage assay" is useful in identifying compounds of this invention. Such a breakage assay step involves reacting a test compound with both subunits of the topoisomerase enzyme and polynucleotide in a suitable buffer, as described above, to allow the ternary complex to form. The reaction may be quenched after about 1 to 60 minutes, by adding a the reaction with a denaturant. Among useful denaturants are detergents, such as sodium dodecyl sulfate. Treatment with the denaturant traps intermediates in which the polynucleotide is in the cleaved state. After the reaction is quenched, a gel analysis is performed conventionally on the products to indicate if the polynucleotide is uncleaved or uncleaved. If uncleaved, that test compound is selected as useful in the methods of this invention.

In still another embodiment of screening methods to identify useful compounds of this invention, the screening assay can also employ a replication blockage assay step. This step is based upon the configuration of a replication assay which is topoisomerase-independent. In such a replication elongation assay, an early replication intermediate is formed by initiating replication on a superhelical polynucleotide template in the absence of any topoisomerase. The resulting replication intermediates formed 'pause' after about 600 nucleotides due to accumulation of positive overwindings in the template. Additional elongation can be monitored by releasing the topological constraint with a restriction enzyme. This replication 'run-off' does not require the presence of a topoisomerase. (Hiasa, H., Marians, K. J. (1994) J. Biol. Chem. 269, 16371–16375.)

The test compound, e.g., the compounds identified specifically above, have no effect upon this reaction to produce 'run-off' products, showing that the replication machinery itself is not affected by the test compounds. However, when the topoisomerase, polynucleotide substrate, and test compound are added together, in any desired order, inhibition of the 'run-off' products is observed, indicating that the polynucleotide-compound-topoisomerase complex is able to inhibit replication, even though the topoisomerase is not required for the reaction. Hence, stabilization of the ternary complex forms a replication block. Test compounds identified as forming a replication block according to this assay step are also selected. for use in the methods and compositions of this invention.

Alternatively, in addition to the replication blocking screening method performed as described above, novel test compounds can be screened for cross-reactivity or competition with the specifically identified compounds of the invention in competition assay demonstrating inhibition of the type II topoisomerase activity, using conventional competition assays.

It is obvious to one of skill in the art that modifications to the assay steps described above, or alternatively designed assays may be employed to screen for the topoisomerase modulating activity identified by the inventors. Given the disclosure of this specification, such assay modifications are considered to be readily selectable by one of skill in the art given known assay information, and thus encompassed by this invention.

Once compounds useful in modulating topoisomerase cleavage of the polynucleotide gsubstrate are identified as described above, such compounds are readily prepared conventionally by known chemical synthesis techniques. Among such preferred techniques known to one of skill in the art are included the synthetic methods described by Merrifield, *J. Amer. Chem. Soc.*, 85:2149–2154 (1963), and other more recent texts, oras detailed in Example 1. Alternatively, the compounds of this invention, where appropriate, may be prepared by known recombinant DNA techniques by cloning and expressing within a host microorganism or cell a DNA fragment carrying a nucleic acid sequence encoding one of the above-described compounds. Coding sequences for these compounds can be prepared synthetically [W. P. C. Stemmer et al, *Gene*, 164:49 (1995)]. Coding sequences can be derived from bacterial RNA by known techniques, or from available cDNA-containing plasmids. Conventional molecular biology techniques, and site-directed mutagenesis may be employed to provide desired compound sequences. Nucleic acid sequences encoding tnese compounds may be used in cloning and expressing the compound compositions of this invention in various host cells well known in recombinant technology, e.g., various strains of *E. coli*, Bacillus, Strepromyces, and Saccharomyces, mammalian cells, (such as Chinese Hamster ovary cells (CHO) or COS-1 cells), yeast and insect cells or viral expression systems, such as baculovirus systems. The selection of other suitable host cells and methods for transformation, culture, amplification, screening and product production and purification can be performed by one of skill in the art by reference to known techniques. See, e.g., Gething and Sambrook, *Nature*, 293:620–625 (1981). When produced by conventional recombinant means, the compounds of this invention may be isolated either from the host cell by conventional lysis techniques or from cell medium by conventional methods, such as chromatography. See, e.g., Sambrook et al, *Molecular Cloning. A Laboratory Manual.*, 2d ed., Cold Spring Harbor Laboratory, New York (1989).

Still another way to identify compounds of this invention involves identifying and selecting compounds which have structural similarity to the test compound, and determining the crystalline structure thereof. The crystalline structure may then be analyzed to design other chemical entities which share the topoisomerase modulating activity of the original compounds. For example, a compound of this invention may be computationally evaluated and designed by means of a series of steps in which chemical entities or fragments are screened and selected for their ability to mimic the biological activity of other compounds of this invention, e.g., the compounds identified above. One skilled in the art may use one of several methods to screen chemical entities or fragments for their ability to mimic the structure of a compound of the invention (or other) compounds of the invention, and more particularly to identify the compound structure that responsible for the topoisomerase modulating activity. This process may begin by visual inspection of, for example, a three dimensional structure of the compounds of this invention on the computer screen. Selected fragments or chemical entities may then be positioned in a variety of orientations to determine structural similarities, or docked, within a putative binding site of the compound.

Specialized computer programs that may also assist in the process of selecting fragments or chemical entities similar to the compounds known or selected by the assays above to have topoisoreerase modulating activity, include the GRID program available from Oxford University, Oxford, UK. [P. J. Goodford, "*A Computational Procedure for Determining Energetically Favorable Binding Sites on Biologically Important Macromolecules*", J. Med. Chem., 28:849–857 (1985)); the MCSS program available from Molecular Simulations, Burlington, Mass. [A. Miranker and M. Karplus, "*Functionality Maps ofBinding Sites: A Multiple*

Copy Simultaneous Search Method", *Proteins: Structure, Function and Genetics*, 11:29–34 (1991)]; the AUTODOCK program available from Scripps Research Institute, La Jolla, Calif. [D. S. Goodsell and A. J. Olsen, "*Automated Docking of Substrates to Proteins by Simulated Annealing*", *Proteins: Structure, Function, and Genetics*, 8:195–202 (1990); and the DOCK program available from University of California, San Francisco, Calif. [I. D. Kuntz et al, "*A Geometric Approach to Macromokcule-Ligand Interactions*", *J. Mol. Biol.*, 161:269–288 (1982)], software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database [for a review see Rusinko, A., *Chem. Des. Auto. News*, 8:44–47 (1993)].

Once suitable chemical entities or fragments have been selected, they can be assembled into a single compound or topoisomerase inhibitor. Assembly may proceed by visual inspection of the relationship of the fragments to each other on the three-dimensional image displayed on a computer screen in relation to the structure of the compound. Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc. 78,pp. 182–196 (1989)], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", *J. Med. Chem.*, 35:2145–2154 (1992)]; and the HOOK program, available from Molecular Simulations, Burlington, Mass.

Compounds that mimic a compound of this invention may be designed as a whole or "de novo" using methods such as the LUDI program [H.-J. Bohm, "The Computer Program LUDI: A New Method for the De Novo Design of Enzyme Inhibitors", *J. Comp. Aid. Molec. Design*, 6:61–78 (1992)], available from Biosym Technologies, San Diego, Calif.; the LEGEND program [Y. Nishibata and A. Itai, *Tetrahedron*, 47:8985 (1991)], available from Molecular Simulations, Burlington, Mass.; and the LeapFrog program, available from Tripos Associates, St. Louis, Mo. Other molecular modeling techniques may also be employed in accordance with this invention. See, e.g., N. C. Cohen et al, "Molecular Modeling Software and Methods for Medicinal Chemistry", *J. Med. Chem.*, 33:883–894 (1990). See also, M. A. Navia and M. A. Murcko, "The Use of Structural Information in Drug Design", *Current Opinions in Structural Biology*, 2:202–210 (1992). For example, where the structures of a variety of compounds to be tested against the known topoisomerase modulators, such as the compounds specifically identified above are themselves known, a model of the a selected compound may be superimposed over the model of a compound of the invention. Numerous methods and techniques are known in the art for performing this step, any of which may be used. See, e.g., P. S. Farmer, *Drug Design*, Ariens, E. J., ed., Vol. 10,pp 119–143 (Academic Press, New York, 1980); U.S. Pat. No. 5,331,573; U.S. Pat. No. 5,500,807; C. Verlinde, *Structure*, 2:577–587 (1994); and I. D. Kuntz, *Science*, 257:1078–1082 (1992). The model building techniques and computer evaluation systems described herein are not a limitation on the present invention.

Thus, using these computer evaluation systems, a large number of topoisomerase modulating compounds may be quickly and easily examined. Thus, expensive and lengthy biochemical testing can be avoided in the identification and selection of other compounds useful in this invention. Moreover, the need for actual synthesis of many compounds is effectively eliminated.

Once identified by the modeling techniques, the proposed topoisomerase modulating compound may be tested for bioactivity using the assays described above. The compound may then be screened for anti-cancer, antineoplastic and antiproliferative efficacy and/or metabolic stability by in vitro and in vivo assays, such as those described in the examples and in the art. Suitable assays for use herein include, but are not limited to, the assays shown below in the examples to detect the antineoplastic effect of the compounds of this invention. However, other assay formats may be used and the assay formats are not a limitation on the present invention.

Pharmaceutical Compositions

Pharmaceutical compositions of this invention are designed to treat neoplasia by an aberrant cell, e.g., human, or to treat a disease the progression of which relies on the activity of a mammalian type II topoisomerase, such as a cancer. At least one, or alternatively, several of the compounds of the present invention may be formulated into an anti-aberrant cell or an anti-tumor composition with a pharmaceutically acceptable carrier and other optional components. For use in such compositions, the selected compound may be produced preferably synthetically, but also recombinantly, as disclosed above.

Compositions are also provided comprising a compound of the invention and another antineoplastic agent, preferably an antineoplastic agent that acts by a mechanism other than topoisomerase.

Compounds that may be combined with a compound of the invention include, but are not limited to alkylating agents, nitrogen mustards (such as, mechlorethamine hydrochloride, cyclophosphamide, ifosfamide, melphalan, chlorambucil, thiotepa, and busulfan), nitrosoureas (such as, carmustine, lomustine, carmustine, and dacarbazine), antimetabolites (such as, methotrexate), pyrimidine analogs (suchas, cytarabine and fluorouracil), purine analogs (such as, mercaptopurine), vinca alkaloids (such as, vincristine sulfate and vinblastine sulfate), taxol, etoposide, doxorubicin hydrochloride, mitoxantrone hydrochloride, bleomycin sulfate, plicamycin, mitomycin, L-asparaginase, platinum coordination complexes (such as, cisplatin), mitotane, hydroxyurea, procarbazine hydrochloride, diethylstilbestrol, estradiol cypionate, and prednisone.

A method of treatment is provided comprising the step of contacting the patient to be treated with a composition comprising compound of the invention and another antineoplastic agent, preferably an antineoplastic agent that acts by a mechanism other than topoisomerase.

The compounds may be employed in pharmaceufical compositions individually. Alternatively, for the purposes of enhancing pharmacokinetics or bioavailability without eliciting immune responses, one or more compounds may be fused or conjugated to other moieties, e.g., carrier proteins or other chemical moieties to enhance stability or delivery, to improve the production, or to change the activity spectrum of the compound. As a few well-known examples, such moieties may be human albumin, polyethylene glycol, biopolymers or other naturally or non-naturally occurring polymers. In one embodiment, the moiety is desirably a molecule which can enhance the stability of the compound.

One of skill in the art can readily select an appropriate conjugation moiety. For the same purposes, one or more of the compounds may be designed as a synthetic compound fused to a carrier protein or other molecule. Still alternatively multiple of the above-described compounds may be combined in a multicompound composition. The compounds of this multi-composition may be coupled to the same carrier, or different compounds may be coupled individually as compounds to the same or a different immunologically inert carrier proteins.

As pharmaceutical compositions, these compositions are admixed with a pharmaceutically acceptable vehicle or carrier suitable for administration. These compounds may be combined in a single pharmaceutical preparation for administration. Suitable pharmaceutically acceptable or physiologically acceptable carriers for use in a pharmaceutical composition of the invention are well known to those of skill in the art. Such carriers include, for example, saline, buffered saline, liposomes, oil in water emulsions and others. The compositions may further include a detergent to make the compound more bioavailable, e.g., octylglucoside. The present invention is not limited by the selection of the carrier or detergent.

Pharmaceutical compositions of this invention may contain other active agents, such as conventional antineoplastic agents or anti-aberrant cell compounds. Where the pharmaceutical composition is intended for and-tumor use, the composition may contain other chemotherapeutic reagents, or be designed for co-administration with other anti-cancer therapies, e.g., chemotherapy, radiation therapy, and the like.

The pharmaceutical compositions may also be formulated to suit a selected route of administration, and may contain ingredients specific to the route of administration [see, e.g., Remington: The Science and Practice of Pharmacy, Vol. 2, 19$^{th}$ edition (1995)]. The preparation of these pharmaceutically acceptable compositions, from the above-described components, having appropriate pH isotonicity, stability and other conventional characteristics is within the skill of the art.

Some of the compounds of this invention may be crystallized or recrystallized from solvents such as organic solvents. In such cases solvates may be formed. This invention includes within its scope stoichiometric solvates including hydrates as well as compounds containing variable amounts of water that may be produced by processes such as lyophilization.

Since the compounds of the invention are intended for use in pharmaceutical compositions it will readily be understood that they are each provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula set forth herein or salt thereof.

Pharmaceutically acceptable derivatives of the above-mentioned compounds of formula set forth herein include the free base form or their acid addition or quatemary ammonium salts, for example their salts with mineral acids e.g. hydrochloric, hydrobromic or sulphuric acids, or organic acids, e.g., acetic, fumaric or tartaric acids. Compounds of formula set forth herein may also be prepared as the N-oxide.

Certain of the above-mentioned compounds of formula set forth herein may exist in the form of optical isomers, e.g. diastereoisomers and mixtures of isomers in all ratios, e.g. racemic mixtures. The invention includes all such forms, in particular the pure isomeric forms. For example, the invention includes compounds in which an A-B group CH(OH)—CH$_2$ is in either isomeric configuration.

Methods of the Invention

One method of modulating the activity of a type II topoisomerase enzyme disclosed by this invention involves contacting the enzyme with a compound of this invention that inhibits enzyme-mediated cleavage of a polynucleotide with which the enzyme is in complex. As noted above, this method may involve the step of stabilizing the complex formed between the enzyme and the uncleaved polynucleotide. Alternatively, the method may employ a step of preventing the formation of the enzyme-uncleaved polynucleotide complex in the first instance. Depending on the use to which the modulating activity is directed, the enzyme in question can a mammalian type II topoisomerase enzyme, preferably a human type II topoisomerase enzyme.

Where the enzyme is a DNA topoisomerase, the contacting step permits the compound to inhibit or kill the aberrant cell having the topoisomerase.

This method can be practiced in vitro to inhibit or kill neoplastic cell growth in tissue cultures or cell cultures in laboratory test tubes, for example. Such in vitro methods may involve the use of the compound and method of the invention for removing cancer cells from ex vivo specimens, such as transplant tissue.

Alternatively, the method may employ the contacting step in vivo. For example, the method may involve treating a mammalian subject for a neoplasia or treating mammalian tissue or cells to eliminate neoplasia The method may also be performed ex vivo, on mammalian tissue treated outside of the body for later reintroduction into the body. The practice of this method according to this embodiment of the invention enables contact with the compound to inhibit or kill an aberrant cell possessing a topoisomerase.

The modulating method of this invention also encompasses contacting the enzyme with a compound of the invention in instances wherein the enzyme is associated with a mammalian disease, and wherein the inhibitory action of the compound retards progression of a disease mediated by the type II topoisomerase. Among such diseases are a variety of cancers as known in the art. Again, for such treatment of disease other than a neoplasia, the contacting step occurs in vivo or ex vivo. In vitro methods may involve the study or research of disease in tissue outside of the body.

A method of treating a mammalian aberrant cell involves administering to a mammal suspected of having cancer with an effective anti-aberrant cell amount of a pharmaceutical composition described above. A method of treating a mammalian cancer or tumor involves administering to an affected mammal an effective anti-tumor amount of a pharmaceutical composition described above. The amount of the compound of the invention present in each anti-aberrant cell or anti-tumor effective dose is selected with regard to consideration of the aberrant cell causing the neoplasia or type of tumor or cancer, the severity of neoplasia or disease, the patient's age, weight, sex, general physical condition and the like. The amount of active component required to induce an effective type II topoisomerase inhibitory effect without significant adverse side effects varies depending upon the pharmaceutical composition employed and the optional presence of other components, e.g., chemotherapeutics and the like.

Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

Other dosage ranges may also be contemplated by one of skill in the art For example, dosages of the compounds of this invention may be similar to the dosages discussed for other antineoplastic agents. Such dosages may be calculated based on the number of neoplastic cells estimated to be involved in the disease. Initial doses of the compounds of this invention may be optionally followed by repeated administration for a duration selected by the attending physician. Dosage frequency may also depend upon the factors identified above, and may range from 1 to 6 doses per day for a duration of about 3 days to a maximum of no more than about 1 week.

According to this invention, a pharmaceutical composition as described above may be administered by any appropriate route, but preferably by a route that transmits the compound directly into the blood, e.g., intravenous injection. Other routes of administration include, without limitation, oral, intradermal, transdermal, intraperitoneal, intramuscular, intrathecal, subcutaneous, mucosal (e.g., intranasal), and by inhalation.

The following examples illustrate various aspects of this invention. While certain of these Examples make use of bacterial enzymes to illustrate a mechanism of action provided by the invention to be acting in eukaryotic topoisomerase reactions. These examples do not limit the scope of this invention which is defined by the appended claims.

EXAMPLE 1

[2S]-1-Heptyl-4-[2-(R,S)-hydroxy-2-(6-methoxyquinoun-4-yl)ethyl]-2-hydroxymethylpiperazine (a) [2S]-Piperazine-2-carboxylic acid di-(S)-camphor-10-sulfonic acid salt This was prepared from [2R,S]-piperazine-2-carboxylic acid dihydrochloride by the method of K. Stingl et al. [*Tetrahedron: Asymmetry*, 8, 979–982 (1997)] and had >99% enantiomeric excess (ee) by chiral HPLC.

(b)[2S]-1-Benzyloxycarbonyl-4-t-butoxycarbonyl-2-methoxycarbonylpiperazine

A solution of [2S]-1-benzyloxycarbonyl-4-t-butoxycarbonylpiperazine-2-carboxylic acid [prepared from Example 1(a) by the method of Bigge et al. *Tet. Letters* 30, 5193 (1989)] (16 g) in methanol (5 ml) and acetonitrile (50 ml) was treated with diisopropylethylamine (5.7 ml) and a 2M solution of trimethylsilyidiazomethane in hexane (26.3 ml) and stirred overnight at room temperature. The reaction mixture was evaporated and chromatographed on silica gel eluting with 0–10% ethyl acetate-hexane to afford the title compound as a colourdess oil (9.0 g).

MS (+ve ion electrospray) m/z 379 (MH+).

(c) [2S]-4-t-Butoxycarbonyl-2-methoxycarbonylpiperazine

A solution of Example 1(b)(4.39 g) in methanol (50 ml) was hydrogenated over 10% palladium on carbon (0.50 g) until uptake of hydrogen ceased. It was filtered and evaporated to afford the title compound as a colourless oil.

MS (+ve ion electrospray) m/z 245 (MH+)

(d) [2S]-4-t-Butoxycarbonyl-2-hydroxymethylpiperazine

A solution of Example 1 (c) in dry tetrahydrofuran (40 ml) at 0° C. was treated with lithium aluminum hydride (0.50 g) and the mixture was stirred at 0° C. for 1.5 hours. The cooled solution was treated dropwise with a solution of 2M sodium hydroxide until a white precipitate had formed. Dichloromethane and anhydrous sodium sulfate were added and the solution was filtered and evaporated to give a pale yellow oil (3.0 g).

MS (+ve ion electrospray) m/z 217 (MH+).

(e) [2S]-4-t-Butoxycarbonyl-1-heptyl-2-hydroxymethylpiperazine

A solution of Example 1(d) (25 ml) was treated with anhydrous potassium carbonate (1.76 g) and n-heptyl iodide (2.88 g) and stirred at room temperature for 18 hours. The 1)1 mixture was evaporated to dryness, treated with sodium carbonate solution, extracted with dichloromethane, dried, and chromatographed on silica gel eluting with 30–50% ethyl acetate-hexane to afford a pale yellow oil (1.5 g) with ee >98% by chiral HPLC [Chirapak AD column; with hexane-ethanol (97:3)].

MS (+ve ion electrospray) m/z 315 (MH+).

(f) [R,S]-2-(6-Methoxyquinolin-4-yl)oxirane

A solution of 6-methoxyquinoline4-carboxylic acid (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyidiazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). This was reduced by treatment with sodium borohydride (0.27 g) in methanol (40 ml) and water (2 ml). The product was extracted with dichloromethane and evaporated to dryness. It was treated with potassium hydroxide (2.9 g) in ethanol (10 ml) and tetrahydrofuran (100 ml). The reaction mixture was diluted with ethyl acetate, washed with water, dried and evaporated. The product was chromatographed on silica gel eluting with ethyl acetate to give the title compound as a solid (2.3 g).

MS (+ve ion electrospray) m/z 202 (MH+).

(g) Title compound

A solution of Example 1(e) (0.53 g) in dichloromethane (20 ml) and trifluoroacetic acid was stirred at 0° C. for 30 minutes and allowed to warm to room temperature over 2 hours. It was evaporated to dryness and azeotroped with toluene to afford [2S]-1-heptyl-2-hydroxymethylpiperazine trifluoroacetate salt as a foam. The salt was dissolved in acetonitrile (3 ml), and treated with diisopropylethylamine (0.544 g) until pH 6. Example 1(f) (0.509 g) and lithium perchlorate (0.179 g) were added and the mixture was stirred at room temperature for 48 hours. [method of J. E. Chateauneuf et al. *J. Org. Chem.* 56, 5939–5942]. The reaction mixture was evaporated and basified with sodium carbonate solution and extracted (×3) with dichloromethane. The organic fraction was dried and chromatographed on silica gel eluting with 50–100% ethyl acetate-hexane to afford the title compound as an oil (0.248 g).

MS (+vc ion electrospray) mnz 416 (MH+).

EXAMPLE 2

[2R]-1-Heptyl-4-[2-(R,S)-hydroxy-2-(6-methoxyquinolin-4-yl)ethyl]-2-hydroxymethylpiperazine (a) [2R]-Piperazine-2-carboxylic acid di-(R)-camphor-10-sulfonic acid salt This was prepared from [2R,S]-piperazine-2-carboxylic acid dihydrochloride by the method of K. Stingi et al.

[*Tetrahedron: Asymmetry*, 8, 979–982 (1997)] using (R)-camphor-10-sulfonic acid and had cc >99% by chiral HPLC [Nucleosil Chiral-1 column]

(b) Title compound

[2R]-Piperazine-2-carboxylic acid di-(R)-camphor-10-sulfonic acid salt was converted to [2R]-4-t-butoxycarbonyl-1-heptyl-2-hydroxymethylpiperazine by the method of Example 1(b-e). Deprotection of a sample (0.38 g) with trifluoroacetic acid in dichloromethane, followed by reaction with Example 1(f)(0.36 g) by the method of Example 1(g) gave an oil (0.275 g).

MS (+ve ion electrospray) m/z 416 (MH+).

EXAMPLE 3

[2S]-1-Heptyl-4-[2-(R)-hydroxy-2-(6methoxyquinolin-4-yl)ethyl]-2-hydroxymethylpiperazine dioxalate[SB-366676-AY)]

(a) [R]-2-(6-Methoxyquinolin-4-yl)oxirane

This was prepared from 6-methoxyquinoline-4-carboxylic acid by the method of Example 1(f) except that the chloromethylketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC). Recrystallisation from ether-pentane gave mother-liquor (7.0 g) (90% ee).

MS (+ve ion electrospray) m/z 202 (MH+)

The absolute stereochemistry was defined to be (R) by an NMR study on the Mosher's esters derived from the product obtained by reaction with 1-t-butylpiperazine.

Reaction of Example 3(a) (0.1 g) and [S]-1-heptyl-2-hydroxymethylpiperazine (0.106 g), by the method of Example 1(g), gave the title compound (0.1 g), as an oil with 90% ee.

MS (+ve ion electrospray) m/z 416 (MH+)

The oil was treated with 2 molar equivalents of oxalic acid in ether and the resulting solid was collected, triturated with ether, to afford the dioxalate salt as a white solid.

EXAMPLE 4

[2S]-2-Carboxymethyl-1-heptyl-4-[2-(R,S)-hydroxy-2-(6-methoxyquinolin-4-yl)ethyl]piperazine trihydrochloride [SB-369890-R]

(a) [2S]-1-Benzyloxycarbonyl-4-t-butoxycarbonyl-2-methoxycarbonylmethylpiperazine A solution of [2R]-1-benzyloxycarbonyl4-t-butoxycarbonylpiperazine-2-carboxylic acid (prepared as in Example 1(b) and 2(a)) (4.7 g) in ethyl acetate (70 ml) containing N-methylmorpholine (1.76 ml) at 0° C. was treated with isobutyl chloroformate (2.37 ml) for 3 hours and the solution was filtered and added to an excess of diazomethane and left at room temperature for 18 hours. It was evaporated to dryness to afford the diazoketone, which was dissolved in dry methanol (120 ml) and treated with silver benzoate (1.99 g) in triethylamine (19.9 ml), with cooling in ice. The solution was stirred in the dark at room temperature for 18 hours, evaporated to dryness, dissolved in ethyl acetate, washed with sodium bicarbonate solution and dried over sodium sulfate. It was chromatographed on silica gel, eluting with ethyl acetate-hexane to afford an oil (3.15 g) (94% ee by chiral HPLC). (b) [2S]4-t-Butoxycarbonyl-1-heptyl-2-methoxycarbonylmethylpiperazine Example 4(a) was hydrogenated over 10% palladium-carbon in methanol and the product reacted with n-heptyl iodide by the method of Example 1(e) to afford an oil.

MS (+ve ion electrospray) m/z 357 (MH+).

(c) [2S]-1-Heptyl-2-methoxycarbonylmethylpiperazine

Example 4(b) (1.05 g) was reacted with trifluoroacetic acid (30 ml) in dichloromethane (30 ml) at room temperature for 2.5 hours and evaporated to dryness. Basification with sodium carbonate and extraction with dichloromethane gave the free base as an oil (0.79 g). (d) [2S]-2-Methoxycarbonylmethyl-1-heptyl-4-[2-(R,S)hydroxy-2-(6-methoxyquinolin-4-yl)ethyl]piperazine This was prepared from Example 4(c) (0.75 g) and Example 1(f) (0.88 g) and lithium perchlorate and the mixture were stirred at room temperature for 24 hours. It was evaporated and basified with sodium carbonate solution and extracted (×3) with chloroform. The organic fraction was dried and chromatographed on silica gel eluting with ethyl acetate-hexane (1:1) followed by methanol-ethyl acetate (5:95) to afford to afford an oil (0.89 g).

MS (+ve ion electrospray) m/z 458 (MH+).

(e) Title compound

A solution of Example 4(d) (0.6 g) was heated in 5M hydrochloric acid (200 ml) for 10 hours and evaporated to dryness to afford a foam (0.8 g).

MS (+ve ion electrospray) m/z 444 (MH+).

EXAMPLE 5

1-Hydroxyheptyl4-[2-(R)-hydroxy-2-(6-methoxyquinolin-4-yl)ethyl]piperazine [SB414468]

The title compound was prepared by procedures analogous to those described herein.

EXAMPLE 6

Biological data: Novel Mechanisms of Action

The above-defined compounds are an exemplary class of compounds, which display the attributes of the claimed compounds of this invention, that is, they act primarily by inhibition of topoisomerase. While the compounds and methods of the invention are directed to eukaryotic, particularly mammalian topoisomerase inhibition, bacterial DNA gyrase was used to illustrate the mechanism of action. The evidence, provided by bacterial enzyme, for such biological activity includes the fact that selective resistance to the compounds is associated with point mutations in Staphylococcus aureus GyrA and B subunits. Further, *Escherichia coli* and *S. aureus* DNA gyrase supercoiling activity is inhibited in vitro by the compounds. A ternary complex has been isolated which is composed of pBR322 relaxed circular DNA, *S. aureus* DNA gyrase, and test compounds. However, these compounds were shown to have a mechanism of action distinct from clastogenic gyrase inhibitors, based upon the lack of cross resistance between the compounds and certain clastogenic compounds in resistant mutants of *S. aureus*. Unlike quinolones (a clastogenic antibiotic), the compounds of the invention do not induce gyrase-mediated DNA breakage, indicating that they do not inhibit the DNA relegation step of the catalytic cycle. The compounds of the invention also show antagonism of ciprofloxacin-induced cleavage of linear DNA. Unlike quinolones, these compounds do not stimulate DNA dependent ATPase activity in DNA gyrase.

These observations indicate that the compounds of the invention inhibit DNA replication by stabilizing a ternary complex of compound+gyrase+uncleaved DNA. Inhibition of gyrase is predicated upon stabilization of a complex in which the DNA is uncleaved.

To demonstrate that compounds of the invention do not induce gyrase-mediated DNA breakage, the effects of the anti-bacterial quinolone compound, ciprofloxacin, on *E. coli* DNA gyrase-mediated DNA cleavage was compared with that of two exemplary compounds, SB208717 and SB362569.

Briefly described, supercoiled pBR322 (Lucent Ltd., University of Leicester, UK.] was cut with EcoR1 to prepare linear pBR322. 0.5 μg linear plasmid pBR322 (8.5 nM) was incubated with 5 units *E. coli* DNA gyrase (12.5 nM) [Lucent Ltd., University of Leicester, UK.] without or with the ciprofloxacin at 0.1 μg/mL, SB208717 at 100 μg/mL or SB362569 at 100 μg/mL at 37 degrees C. in 1× linear buffer. The linear buffer contained 35 mM Tris-HCI, pH 7.5, 24 mm KCl, 4 mm $MgCl_2$, 5 mm DTT, 1.4 mm ATP, 6.5% glycerol, and 0.36 mg/ml bovine serum albumin (BSA). Samples were taken at 30, 60, 120 and 240 minute time intervals and reactions were stopped with 1% SDS. After treatment with proteinase K, samples were separated by gel electrophoresis and the gel stained with ethidium bromide.

The resulting gel showed that gyrase mediated DNA cleavage was induced by ciprofloxacin at 0.1 μg/ml, but not by two test compounds at 100 μg/ml over 4 hours under the conditions tested.

Compounds of the Invention Do Not Induce DNA Cleavage

In further experiments compound-induced DNA cleavage was not observed under the following range of different conditions:

(a) with linear, supercoiled or relaxed DNA substrate (pBR322).
(b) with and without ATP (1.4 mM).
(c) reaction stopped with 0.2%, 1.0% or 2% SDS, 50 mm EDTA or 5M urea;
(d) increased enzyme—4 fold increase to 50 nM—6 fold excess over substrate DNA; and
(e) reactions incubated at room temperature or 37 degrees C.

However, quinolone-induced DNA cleavage was observed under all of these conditions, except when the reaction was stopped with EDTA or urea. Quinolones induce gyrase-mediated DNA breakage, indicating that quinolones inhibit the DNA relegation step of the catalytic cycle. Quinolones also stimulate DNA dependent ATP'base activity in DNA gyrase. The quinolone mechanism of action is the stabilization of the ternary complex of quinolone+gyrase+cleaved DNA at a different stage of the catalytic cycle (cleaved DNA for quinolones vs. uncleaved DNA for compounds of the invention).

Binding Assay Demonstrating Ternary Complex Formation

A binding assay was developed to demonstrate compound binding to the complex between DNA gyrase and pBR322 DNA. An excess of test compound is added, typically as a mixture of three ligands, and after incubation the excess compound is separated from the resulting DNA:gyrase complex using size exclusion chromatography (SEC), with reverse phase HPLC and on-line MS detection to identify and quantify the bound compound.

SB366676-AY was detected in the high molecular weight fraction with clear resolution from excess ligand on the SEC column. Only binding of SB366676-AY ($IC_{50}$=0.2 μM) was detected in the presence of SB369890 ($IC_{50}$=1.0 μM) and BRL26172CC ($IC_{50}$=20 μM) (structure in formula (Ic), below). No complex was demonstrated without both GyrA and B, or without DNA. Stoichiometry studies show that two molecules of SB366676-AY bind to each gyrase:DNA complex.

formula (Ic)

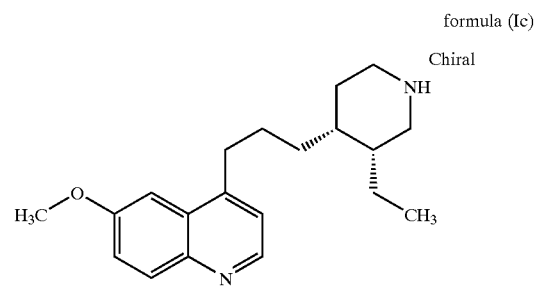

Studies using SEC/MS have demonstrated that oligo-nucleotides between 30 and 300 base pairs will form a ternary complex with compounds of the invention and DNA gyrase. For example, truncated DNA gyrase, such as gyrase lacking an ATPase domain, will form a stable complex with pR322 DNA and compound of the invention.

All documents cited above and patent applications to which priority is claimed are incorporated by reference herein in their entirety. This invention is not to be limited in scope by the specfic embodiments described herein. Indeed, various modifications of the invention in addition to those described herein will become apparent to those skilled in the art from the foregoing description. Such modifications are intended to fall within the scope of the appended claims. The disclosures of the patents, patent applications and publications cited herein are incorporated by reference in their entireties.

What is claimed is:

1. A method of modulating the activity of a mammalian type II topoisomerase enzyme comprising contacting said enzyme with a compound of formula (Ia) or a pharmaceutically acceptable derivative thereof:

(Ia)

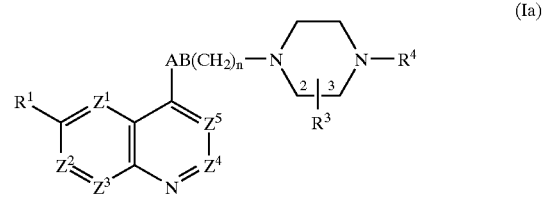

wherein:
one of $Z_1$, $Z^2$, $Z^3$, $Z^4$ and $Z^5$ is N, one is $CR^{1a}$ and the remainder are CH, or one of $Z^1$, $Z^2$, $Z^3$, $Z^4$ and $Z^5$ is $CR^{1a}$ and the remainder are CH;

$R^1$ is selected from hydroxy; $(C_{1-6})$ alkoxy optionally substituted by $(C_{1-6})$alkoxy, amino, piperidyl, guanidino or amnidino optionally N-substituted by one or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$ alkoxy-substituted $(C_{1-6})$alkyl; halogen; $(C_{1-6})$alkyl; $(C_{1-6})$atkylthio; nitro; azido; acyl; acyloxy; acylthio;

(C$_{1-6}$)alkylsulphonyl; (C$_{1-6}$)alkylsulphoxide; arylsulphonyl; arylsulphoxide or an amino, piperidyl, guanidino or amidino group optionally N-substituted by one or two (C$_{1-6}$)alkyl, acyl or (C$_{1-6}$)alkylsulphonyl groups, or when one of $Z^1$, $Z^2$, $Z^3$, $Z^4$ and $Z^5$ is N, $R^1$ may instead be hydrogen;

$R^{1a}$ is selected from H and the groups listed above for $R^1$;

$R^3$ is hydrogen; or $R^3$ is in the 2- or 3-position and is:

carboxy; (C$_{1-6}$)alkoxycarbonyl; aminocarbonyl wherein the amino group is optionally substituted by hydroxy, (C$_{1-6}$)alkyl, hydroxy(C$_{1-6}$)alkyl, aminocarbonyl(C$_{1-6}$) alkyl, (C$_{2-6}$)alkenyl, (C$_{1-6}$)alkylsulphonyl, trifluoromethylsulphonyl, (C$_{1-6}$)alkenylsulphonyl, (C$_{1-6}$)alkoxycarbonyl, (C$_{1-6}$)alkylcarbonyl, (C$_{2-6}$) alkenyloxycarbonyl or (C$_{2-6}$)alkenylcarbonyl and optionally further substituted by (C$_{1-6}$)alkyl, hydroxy (C$_{1-6}$)alkyl, aminocarbonyl(C$_{1-6}$)alkyl or (C$_{2-6}$) alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo1,2,4-oxadiazol-3-yl; or $R^3$ is in the 2- or 3-position and is (C$_{1-4}$)alkyl or ethenyl substituted with any of the groups listed above for $R^3$ and/or 0 to 3 groups $R^{12}$ independently selected from:
thiol; halogen; (C$_{1-6}$)alkylthio; trifluoromethyl; azido; (C$_{1-6}$)alkoxycarbonyl; ( C$_{1-6}$)alkylcarbonyl; (C$_{2-6}$) alkenyloxycarbonyl; (C$_{2-6}$)alkenylcarbony); hydroxy optionally substituted by (C$_{1-6}$)alkyl, (C$_{2-6}$) alkenyl, (C$_{1-6}$)alkoxycarbonyl, (C$_{1-6}$)alkylcarbonyl, (C$_{2-6}$)alkenyloxycarbonyl,(C$_{2-6}$)alkenylcarbonyl or amninocarbonyl wherein the amino group is optionally substituted by (C$_{1-6}$)alkyl, (C$_{2-6}$)alkenyl, (C$_{1-6}$) alkylcarbonyl or (C$_{2-6}$)alkenylcarbonyl; amino optionally mono- or disubstituted by (C$_{1-6}$) alkoxycarbonyl, (C$_{1-6}$)alkylcarbonyl, (C$_{2-6}$) alkenyloxycarbonyl, (C$_{2-6}$)alkenylcarbonyl, (C$_{1-6}$) alkyl, (C$_{2-6}$)alkenyl, (C$_{1-6}$)alkylsulphonyl, (C$_{2-6}$) alkenylsulphonyl or aminocarbonyl wherein the amino group is optionally substituted by (C$_{1-6}$)alkyl or (C$_{2-6}$)alkenyl; aminocarbonyl wherein the amino group is optionally substituted by (C$_{1-6}$)alkyl, hydroxy(C$_{1-6}$)alkyl, aminocarbonyl(C$_{1-6}$)alkyl, (C$_{2-6}$)alkenyl, (C$_{1-6}$)alkoxycarbonyl, (C$_{-6}$) alkylcarbonyl, (C$_{2-6}$)alkenyloxycarbonyl or (C$_{2-6}$) alkenylcarbonyl and optionally further substituted by (C$_{1-6}$)alkyl, hydroxy(C$_{1-6}$)alkyl, aminocarbonyl (C$_{1-6}$)alkyl or (C$_{2-6}$)alkenyl; oxo; (C$_{1-6}$) alkylsulphonyl; (C$_{2-6}$)alkenylsulphonyl;(C$_{1-6}$) aminosulphonyl wherein the amino group is optionally substituted by (C$_{1-6}$)alkyl or (C$_{2-6}$)alkenyl; provided that when $R^3$ is disubstituted with hydroxy or amino and carboxy containing substituents these may optionally together form a cyclic ester or amide linkage, respectively;

wherein $R^{10}$ is selected from (C$_{1-4}$)alkyl; (C$_{2-4}$)alkenyl; aryl; a group $R^{12}$ as defined above; carboxy; aminocarbonyl wherein the amino group is optionally substituted by hydroxy, (C$_{1-6}$)alkyl, (C$_{2-6}$)alkenyl, (C$_{1-6}$) alkylsulphonyl, trifluoromethylsulphonyl, (C$_{1-6}$) alkenylsulphonyl, (C$_{1-6}$)alkoxycarbonyl, (C$_{1-6}$) alkylcarbonyl, (C$_{2-6}$)alkenyloxycarbonyl or (C$_{2-6}$) alkenylcarbonyl and optionally further substituted by (C$_{1-6}$)alkyl or (C$_{2-6}$)alkenyl; cyano; or tetrazolyl;

$R^4$ is a group —CH$_2$-R$^5$ in which $R^5$ is selected from:
(C$_{3-12}$)alkyl; hydroxy(C$_{3-12}$)alkyl; (C$_{1-12}$)alkoxy (C$_{3-12}$)alkyl; (C$_{1-12}$)alkanoyloxy(C$_{3-12}$)alkyl; (C$_{3-6}$) cycloalkyl(C$_{3-12}$)alkyl; hydroxy-, (C$_{1-12}$)alkoxy- or (C$_{1-12}$)alkanoyloxy-(C$_{3-6}$)cycloalkyl(C$_{3-12}$)alkyl; cyano(C$_{3-12}$)alkyl; (C$_{2-12}$)alkenyl; (C$_{2-12}$)alkynyl; tet or di-(C$_{1-12}$)alkylarnino(C$_{3-12}$)alkyl; acylamino (C$_{3-12}$)alkyl; (C$_{1-12}$)alkyl- or acyl-aminocarbonyl (C$_{3-12}$)alkyl; mono- or di-(C$_{1-12}$)alkylamino (hydroxy)(C$_{3-12}$)alkyl; optionally substituted phenyl (C$_{1-2}$)alkyl, phenoxy(C$_{1-2}$)alkyl or phenyl(hydroxy) (C$_{1-2}$)alkyl; optionally substituted diphenyl(C$_{1-2}$) alkyl; optionally substituted phenyl(C$_{2-3}$)alkenyl; optionally substituted benzoyl or benzoyl(C$_{1-3}$)alkyl; optionally substituted heteroaryl or heteroaryl(C$_{1-2}$) alkyl;and optionally substituted heteroaroyl or heteroaroylmethyl;

n is 0, 1 or2;

AB is NR11CO,CO—CR$^8$R$^9$ or CR$^6$R$^7$—CR$^8$R$^9$ or when n is 1 or 2, AB may instead be O—CR$^8$R$^9$ or NR$^{11}$—CR$^8$R$^9$, or when n is 2 AB may instead be CR$^6$R$^7$—NR$^{11}$ or CR$^6$R$^7$—O, provided that when n is 0, B is not CH(OH), and wherein:
each of $R^6$ and R$^7$R$^8$ and $R^9$ is independently selected from: H; thiol; (C$_{1-6}$)alkylthio; halo; trifluoromethyl; azido; (C$_{1-6}$)alkyl; (C$_{2-6}$)alkenyl; (C$_{1-6}$) alkoxycarbonyl; (C$_{1-6}$)alkylcarbonyl; (C$_{2-6}$) alkenyloxycarbonyl; (C$_{2-6}$)alkenylcarbonyl; hydroxy, amino or arninocarbonyl optionally substituted as for corresponding substituents in $R^3$; (C$_{1-6}$)alkylsulphonyl; (C$_{2-6}$)alkenylsulphonyl; or (C$_{1-6}$)aminosulphonyl wherein the amino group is optionally substituted by (C$_{1-6}$)alkyl or (C$_{1-6}$)alkenyl; or $R^6$ and $R^8$ together represent a bond and $R^7$ and $R^9$ are as above defined; and each $R^{11}$ is independently H, trifluoromethyl, (C$_{1-6}$)alkyl, (C$_{1-6}$)alkenyl, (C$_{1-6}$)alkoxycarbonyl, (C$_{1-6}$)alkylcarbonyl, aminocarbonyl wherein the amino group is optionally substituted by (C$_{1-6}$) alkoxycarbonyl, (C$_{1-6}$)alkylcarbonyl, (C$_{1-6}$) alkenyloxycarbonyl, (C$_{2-6}$)alkenylcarbonyl, (C$_{1-6}$) alkyl or (C$_{1-6}$)alkenyl and optionally further substituted by (C$_{1-6}$)alkyl or (C$_{1-6}$)alkenyl;

or where one of $R^3$ and $R^6$, $R^7$, $R^8$ or $R^9$ contains a carboxy group and the other contains a hydroxy or amino group they may together form a cyclic ester or amide linkage, wherein the said compound inhibits enzyme-mediated cleavage of a polynucleotide substrate.

2. A method of modulating the activity of a mammalian type II topoisomerase enzyme comprising contacting said enzyme with a compound of formula (Ib), wherein said compound is:

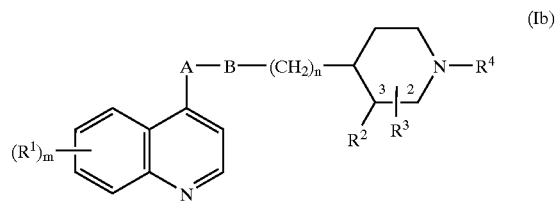

(Ib)

wherein m is 1 or 2 each $R^1$ is independently hydroxy; (C$_{1-6}$) alkoxy optionally substituted by (C$_{1-6}$)alkoxy, amino, piperidyl, guanidino or amidino optionally N-substituted bygone or two $(C_{1-6})$alkyl, acyl or $(C_{1-6})$alkylsulphonyl groups, $NH_2CO$, hydroxy, thiol, $(C_{1-6})$alkylthio, heterocyclylthio, heterocyclyloxy, arylthio, aryloxy, acylthio, acyloxy or $(C_{1-6})$alkylsulphonyloxy; $(C_{1-6})$ alkoxy-substituted $(C_{1-6})$alkyl; halogen; $(C_{1-6})$alkyl; $(C_{1-6})$alkylthio; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups; either $R^2$ is hydrogen; and $R^3$ is in the 2- or 3-position and is hydrogen or $(C_{1-6})$alkyl or $(C_{2-6})$alkenyl optionally substituted with 1 to 3 groups selected from:
   thiol; halogen; $(C_{1-6})$alkylthio; trifluoromethyl; azido; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$ alkylcarbonyl, $(C_{2-6})$alkenyloxycarbonyl,$(C_{2-6})$ alkenylcarbonyl or aminocarbonyl wherein the amino group is optionally substituted by $(C_{1-6})$alkyl, $(C_{2-6})$alkenyl, $(C_{1-6})$aklycarbonyl or $(C_{2-6})$ alkenylcarbonyl; amino optionally mono- or disubstituted by $(C_{1-6})$)alkoxycarbonyl, $(C_{1-6})$ alkylcarbonyl, $(C_{2-6})$alkenyloxycarbonyl, $(C_{2-6})$ alkenylcarbonyl, $(C_{1-6})$alkyl, $(C_{2-6})$alkenyl, $(C_{1-6})$ alkylsulphonyl, $(C_{2-6})$alkenyIsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aniinocarbonyl$(C_{1-6})$alkyl, $(C_{2-6})$alkenyl, $(C_{1-6})$ alkoxycarbonyl,$(C_{2-6})$alkenylcarbonyl and optionally further substituted by $(C_{1-6})$alkyl, hydroxy $(C_{1-6})$alkyl, aminocarbonyl$(C_{1-6})$alkyl or $(C_{2-6})$ alkenyl; oxo; $(C_{1-6})$alkylsulphonyl; $(C_{2-6})$ alkenylsulphonyl; or aminosulphonyl wherein the amino group is optionally substituted by $(C_{1-6})$alkyl or $(C_{2-6})$alkenyl; or $R^3$ is in the 3-position and $R^2$ and $R^3$ together are a divalent residue $=CR^5R^{6^1}$ where $R^{5^1}$ and $R^{6^1}$ are independently selected from H, $(C_{1-6})$alkyl, $(C_{2-6})$alkenyl, aryl$(C_{16})$alkyl and aryl$(C_{2-6})$alkenyl, any alkyl or alkenyl moiety being optionally substituted by I to 3 groups selected from those listed above for substituents on $R^3$;

$R^4$ is a group —$CH_2$-$R^5$ in which $R^5$ is selected from: $(C_{3-12})$alkyl; hydroxy$(C_{3-12})$alkyl; $(C_{1-12})$alkoxy$(C_{3-12})$ alkyl; $(C_{1-12})$alkanoyl-$(C_{3-12})$alkyl; $(C_{3-6})$cycloalkyl $(C_{3-12})$alkyl; hydroxy-, $(C_{1-12})$alkoxy- or $(C_{1-12})$ alkanoyloxy-$_{(3-6)}$cycloalkyl$(C_{3-12})$alkyl; cyano$(C_{3-12})$ alkyl; $(C_{2-12})$alkenyl; $(C_{2-12})$alkynyl; tet or di-$(C_{1-12})$ alkylamino$(C_{3-12})$alkyl; acylamino$(C_{3-12})$alkyl; $(C_{1-12})$ alkyl- or acyl-aminocarbonyl$(C_{1-12})$alkyl; mono- or di-$(C_{1-12})$alkylamino(hydroxy) $(C_{3-12})$alkyl; optionally substituted phenyl$(C_{1-2})$alkyl, phenoxy$(C_{1-2})$alkyl or phenyl(hydroxy)$(C_{1-2})$alkyl; optionally substituted diphenyl$(C_{1-2})$alkyl; optionally substituted phenyl $(C_{2-3})$alkenyl; optionally substituted benzoyl or benzoylmethyl; optionally substituted heteroaryl$(C_{1-2})$ alkyl;and optionally substituted heteroaroyl or heteroaroylmethyl;

n is 0, 1 or 2;

A is $NR^{11},O,S(O)_x$ or $CR^6R^7$ and B is $NR^{11},O,S(O)_x$ or $CR^8R^9$ where x is 0, 1 or 2 and wherein:

each of $R^6$ and $R^7$ $R^8$ and $R^9$ is independently selected from: H; thiol; $(C_{1-6})$alkylthio; halo; trifluoromethyl; azido; $(C_{1-6})$alkyl; $(C_{2-6})$alkenyl; $(C_{1-6})$ alkoxycarbonyl; $(C_{1-6})$alkylcarbonyl; $(C_{2-6})$ alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$amninosulphonyl wherein the amino group is optionally substituted by $(C_1I_6)$alkyI or$(CI6)$alkenyl;

or $R^6$ and $R^8$ together represent a bond and $R^7$ and $R^9$ are as above defined;

or $R^6$ and $R^8$ together represent -O- and $R^7$ and $R^9$ are both hydrogen;

or $R^6$ and $R^7$ or $R^8$ and $R^9$ together represent oxo;

and each $R^{11}$ is independently H, trifluoromethyl, $(C_{1-6})$ alkyl, $(C_{1-6})$alkenyl, $(C_{1-6})$alkoxycarbonyl, $(C_{1-6})$ alkylcarbonyl, aminocarbonyl wherein the amino group is optionally substituted by $(C_{1-6})$ alkoxycarbonyl, $(C_{1-6})$alkylcarbonyl, $(C_{1-6})$ alkenyloxycarbonyl, $(C_{2-6})$alkenylcarbonyl, $(C_{1-6})$ alkyl or $(C_{1-6})$alkenyl and optionally further substituted by $(C_{1-6})$alkyl or $(C_{1-6})$alkenyl;

provided that A and B cannot both be selected from $NR_{11},O$ and $S(O)_x$ and when one of A and B is CO the other is not CO,O or $S(O)_x$, wherein the said compound inhibits enzyme-mediated cleavage of a polynucleotide substrate.

3. A method of modulating the activity of a mammalian type II topoisomerase enzyme comprising contacting said enzyme with a compound, wherein said compound is selected from the group consisting of:

[3R,4R]-3-Ethyl-1-heptyl-4-[3-(R,S)hydroxy-3-(6-methoxyquinolin-4-yl)propyl]piperidine;

[3R,4R]-1-Heptyl-3-(1-(R)hydroxyethyl)-4-[3-(6-methoxyquinolin-4-yl)propyl]piperidine;

[3R,4R]-1-Heptyl-3-hydroxymethyl-4-[3-(6-methoxyquinolin-4-yl)propyl]piperidine;

[2S]-1-Heptyl-4-[2-(R)-hydroxy-2-(6-methoxyquinolin-4-yl)ethyl]-2-hydroxymethyipiperazine;

[2S]-2-Carboxymethyl-1-heptyl-4-[2-(R,S)-hydroxy-2-(6methoxyquinolin-4-yl)ethyl]piperazine trihydrochloride; and 1-Hydroxyheptyl-4-[2-(R)-hydroxy-2-(6-methoxyquinolin-4-yl)ethyl]piperazine, wherein the said compound inhibits enzyme-mediated cleavage of a polynucletoide substrate.

* * * * *